United States Patent [19]
Anderson et al.

[11] 3,953,532
[45] Apr. 27, 1976

[54] 4,8-TRIDECADIEN-1-OL,4 CIS,8 CIS,TRANS
[75] Inventors: Richard J. Anderson; Clive A. Henrick, both of Palo Alto, Calif.
[73] Assignee: Zoecon Corporation, Palo Alto, Calif.
[22] Filed: Apr. 14, 1975
[21] Appl. No.: 567,907

Related U.S. Application Data
[62] Division of Ser. No. 463,938, April 25, 1974, Pat. No. 3,919,329.

[52] U.S. Cl............................................. 260/632 R
[51] Int. Cl.² ........................................ C07C 33/02
[58] Field of Search ................................ 266/632 R

[56] References Cited
UNITED STATES PATENTS
3,072,526  1/1963  Butenandt et al............... 260/632 R
3,783,135  1/1974  Henrick et al. ................. 260/632 R

OTHER PUBLICATIONS

Butenandt et al., "Chem. Abstracts", Vol. 56 (1962), columns 7811, 7812.

Crombie et al., "Chem. Abstracts", Vol. 50 (1956), columns 13001–13003.

Primary Examiner—Joseph E. Evans
Attorney, Agent, or Firm—Donald W. Erickson

[57] ABSTRACT

Synthesis of the sex pheromone, (7Z,11Z/E)-7,11-hexadecadienyl acetate, of the pink bollworm moth, *Pectinophora gossypiella*, and intermediates therefor.

1 Claim, No Drawings

4,8-TRIDECADIEN-1-OL,4 CIS,8 CIS,TRANS

This is a division of application Ser. No. 463,938, filed April 25, 1974, now U.S. Pat. No. 3,919,329.

This invention relates to the synthesis of the sex pheromone, (7Z,11Z/E)-7,11-hexadecadienyl acetate, of the female pink bollworm moth, *Pectinophora gossypiella* (Saunders) and intermediates therefor.

The sex pheromone of the female pink bollworm moth has been identified as a mixture of cis,cis and cis,trans isomers of 7,11-hexadecadienyl acetate, Hummel et al, Science 181, 873 (31 August 1973). The authors found that a 1:1 mixture of the cis,cis and cis,-trans isomers was an effective attractant for capturing male moths in a field-trap evaluation whereas the cis,-cis isomer alone and cis,trans isomer alone were apparently ineffective attractants.

The present invention provides means for the synthesis of isomers of 7,11-hexadecadienyl acetate, the preparation of isomeric mixtures thereof, and intermediates therefor.

The synthesis of this invention is outlined as follows:

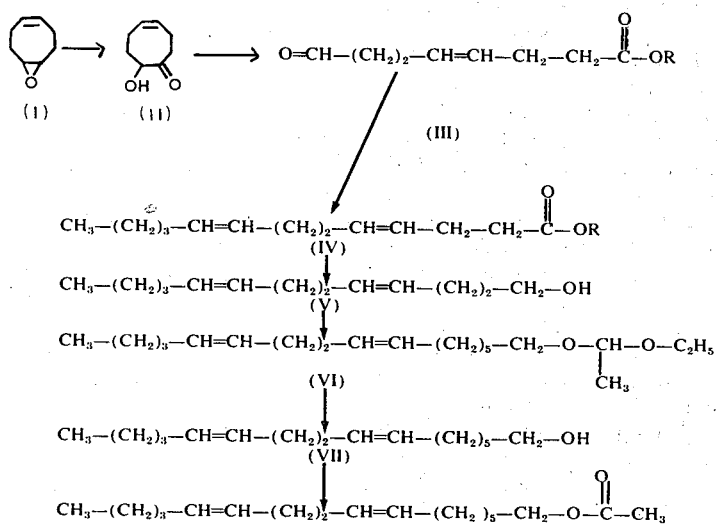

In the practice of the above outlined synthesis, 1,5-cyclooctadiene is oxidized using organic peracid to the 1,2-epoxy-5-cyclooctene (I). The epoxide I can be prepared also using t-butylhydroperoxide in the presence of molybodenum catalyst. The oxidation of epoxide I to the α-hydroxyketone II is accomplished by bubbling air through a solution of the epoxide in dimethylsulfoxide at above room temperature for several hours. The oxidative change of 2-hydroxy-5-cyclooct-en-1-one to the aldehyde ester III is carried out using lead tetraacetate in a lower alkanol of one to three carbon atoms (R is lower alkyl of one to three carbon atoms) in the presence of benzene. The aldehyde ester III is then converted by Wittig reaction with triphenylamylphosphonium bromide to the 4,8-tridecadienoic ester IV having cis isomerism at C-4 and cis,trans isomerism at C-8. The isomeric ratio at position C-8 is effected considerably by the solvent, temperature and base of the Wittig reaction as shown in the examples hereinafter. The diene ester IV is reduced to the alcohol V using lithium aluminum hydride. The mixed acetal VI is prepared via copper coupling reaction of the iodide or bromide (VA) which is obtained from the mesylate of V.

$$CH_3\text{-}(CH_2)_3\text{-}CH{=}CH\text{-}(CH_2)_2\text{-}CH{=}CH\text{-}(CH_2)_2\text{-}CH_2\text{-}X$$

The coupling reaction used to prepare the diene acetal VI is carried out using a cuprate reagent prepared from cuprous iodide and the lithium reagent obtained from the reaction of lithium and the bromo-acetal

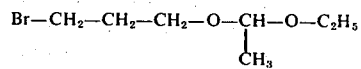

which is obtained from 3-bromo-1-propanol and ethyl vinyl ether. By treatment with aqueous acid the acetal VI is hydrolyzed to 7,11-hexadecadienol which is converted into the acetate using acetic anhydride in pyridine.

Following the examples hereinafter, it is possible to prepare an essentially 1:1 mixture of the 7 cis,11 and 7 cis,11 trans isomers directly through synthesis. In the alternative, a particular isomeric ratio can be prepared by blending the compounds having a different isomeric ratio.

The following examples are provided to illustrate the practice of the invention. Temperature is given in degrees Centigrade.

EXAMPLE 1

A. To an ice bath cooled solution of 21.6 gm. of 1,5-cyclooctadiene in about 400 ml. of methylene dichloride is added, in portions, 41.0 gm. of 85% m-chloroperbenzoic acid, maintaining the temperature at 10°–15°. The suspension is stirred overnight and then filtered. The filtrate is washed with 2M sodium cabonate and saturated sodium chloride solutions and then dried over calcium sulfate. Distillation through Vigreux column yields the monoepoxide (1,2-oxido-5-cyclooctene), b.p. 95–100° (10 mm.).

B. To 20 ml. of dimethylsulfoxide is added 4.5 gms. of the monoepoxide of Part A. Air is bubbled through this solution at 110° for 60 hours. The solution is then poured into ice-saturated sodium chloride and ether. The water layer is separated and extracted twice with ether. The ether extracts are combined with the organic layer and washed twice with saturated sodium chloride and then dried over calcium sulfate. The crude product is applied to six silica plates (1 m. × 20 cm.) impregnated with Rhodamine dye and eluted with 20% ethyl acetate/hexane. Main product band ($R_f$ 0.2) is removed to give 2-hydroxy-5-cycloocten-1-one which distills at 55° at 0.1 mm.

EXAMPLE 2

To 220 mg. of 2-hydroxy-5-cycloocten-1-one in 5 ml. of 30% ethanol/benzene is added 860 mg. of 85% lead tetraacetate in portions. After about 3 hours at room temperature, water and ether are added to the reaction mixture. The aqueous phase is extracted several times with ether. The combined ether extracts are washed with 2M sodium carbonate and saturated sodium chloride solution, dried over calcium sulfate and evaporated to give ethyl (4Z)-8-oxo-4-octenoate in high purity.

EXAMPLE 3

A. To a suspension of 3.47 gm. of triphenyl n-pentyl-phosphonium bromide in 50 ml. of dry ether, under nitrogen, is added 4.8 ml. of 1.67M n-butyllithium in hexane. After about 30 minutes of stirring, the solution is cooled to −40° and then 1.26 gm. of ethyl 8-oxo-4-octenoate in about 5 ml. of ether is added. The suspension is stirred for about 80 minutes and then 40 ml. of ethanol is added slowly (about 5 minutes). After about 10 minutes, the cooling bath is removed and the solution stirred in a water bath (about 30°for one hour. The reaction is worked up using ether/hexane (3/1), washing with brine, drying over calcium sulfate and evaporation of solvent. The residue is treated with pentane and the pentane soluble portion then applied to three silica plates (1 m. × 20 cm., Rhodamine impregnated) which are eluted with 5% ethyl acetate/hexane to yield ethyl (4Z,8Z/E)-4,8-tridecadienoate ( 49:51 cis,trans at C-8).

The phosphonium salt can be prepared as follows: To 125 gm. of triphenylphosphine in about 450 ml. of benzene, under nitrogen, is added 75 gm. of 1-bromopentane. The solution is refluxed for 72 hours. On cooling, the solid mass is broken up, filtered and then washed several times with diethyl ether. The salt is dried under high vacuum.

B. A mixture of 1 gm. of the ester of Part A, 15 ml. of dry ether and 0.6 ml. of 4.3M lithium aluminum hydride, at 20°, is stirred for 3 hours and then quenched with saturated sodium sulfate solution. The reaction is diluted with ether and 2% HCl and the layers separated. The ether phase is washed with saturated sodium bicarbonate and saturated sodium chloride and dried over sodium sulfate. Solvent is removed and the concentrate distilled to yield (4Z,-8Z/E)-4,8-tridecadien-1-ol, b.p. 70° (bath) at 0.05 mm.

C. To a mixture of 746 mg. of the alcohol of Part B, 20 ml. of methylenedichloride, and 555 mg. of triethylamine, stirred and cooled to 0 to −10°, is added 480 mg. of methanesulfonyl chloride, dropwise. After 1.5 hours, ice is added and the layers separated. The organic phase is washed with saturated sodium bicarbonate and saturated sodium chloride, dried over sodium sulfate and solvent removed to yield the mesylate.

D. A mixture of 1 gm. of the mesylate of Part C, 25 ml. of acetone, and 750 mg. of sodium iodide, under nitrogen, is heated at 60° for 20 hours. The reaction is diluted with water and hexane and separated. The aqueous phase is extracted with hexane. The organic phase combined with the hexane extracts is washed with 1% sodium bicabonate and saturated sodium chloride and dried over sodium sulfate. Solvent is removed to yield (4Z,8Z/E)-4,8-tridecadien-1-yl iodide (cis:trans ratio of 49:51 at C-8).

EXAMPLE 4

A. About 17 gm. of 3-bromopropanol is stirred overnight with several grams of sodium carbonate to remove acid components. The suspension is centrifuged and the supernatant 3-bromopropanol removed by pipette (11.6 gm.). To this bromoalcohol is added about 25 ml. of ethylvinyl ether and 100 mg. trichloroacetic acid. After about 1.5 hours, an additional 100 mg. of trichloroacetic acid is added and the reaction stirred for 32 hours. One gm. of solid sodium carbonate is added and then after 24 hours, the reaction is filtered and excess ether removed. The residue is distilled to give the bromo-acetal, b.p. 60.5–62° (3 mm.).

B. To 10 ml. dry ether, under argon, is added about 252 mg. of lithium (containing 1% sodium) in pieces. To this suspension, cooled to 0°, is added 0.5 gm. of the bromo-acetal of Part A in 12 ml. of diethyl ether. After about 10 minutes, additional bromo-acetal (3.3 gm.) in about 10 ml. of diethyl ether is added over about 20 minutes while maintaining temperature at −5 to −10°. Formation of the lithium reagent is complete after about 2 hours (molarity of 0.54M).

To 1.03 gm. of cuprous iodide in 15 ml. of dry tetrahydrofuran, under nitrogen and at −20°, is added 20 ml. of the above lithium reagent. After about 15 minutes, 0.90 gm. of (4Z,8Z/E)-4,8-tridecadien-1-yl iodide in dry tetrahydrofuran is added. After about 1 hour, the reaction is quenched by addition of saturated ammonium chloride and worked up using ether and ammonium chloride solution. The organic phase is washed to neutrality with saturated sodium chloride, dried over calcium sulfate and concentrated. The residue (acetal VI) is dissolved in 30 ml. tetrahydrofuran and 20 ml. water containing 250 mg. trichloroacetic acid. After about 20 hours at room temperature, the reaction is heated to 60° for 1 hour. After cooling, the reaction is worked up by addition of ether and 2M sodium carbonate. The organic phase is washed with saturated sodium chloride and dried over calcium sulfate. After concentration, the residue is applied to two silica plates (1 m. × 20 cm.) impregnated with Rhodamine and eluted in 20% ether/hexane to yield (7Z,11Z/E)-7,11-hexadecadien-1-ol, b.p. 95° (bath) at 0.025 mm.

The acetate is prepared by dissolving 520 mg. of the alcohol in 3 ml. pyridine and 1.5 ml. acetic anhydride and stirring a few hours, under nitrogen. Ice is added to the reaction followed by stirring and addition of hexane/ether (9/1). The organic phase is washed with 5% HCl, 2M sodium carbonate and saturated sodium chloride, dried over calcium sulfate and concentrated. The concentrate is distilled, 80° (bath) at 0.025 mm., to yield (7Z,11Z/E)-7,11-hexadecadienyl acetate (cis:-trans ratio of 49:51 at C-11).

EXAMPLE 5

To a mixture of 40 mg. of sodium hydride (previously washed with pentane), 5 ml. of dry dimethylformamide and 700 mg. of triphenylamylphosphonium bromide, under nitrogen, and at room temperature, is added, dropwise, 180 mg. of ethyl 8-oxo-4-octenoate in 1 ml. of dimethylformamide. After addition is complete, the reaction is stirred for several hours and then quenched with water. The reaction is worked up by extraction with ether, washing with saturated sodium chloride, drying over calcium sulfate, evaporation of solvent and distillation (65° at 0.03 mm.) to yield ethyl (4Z,8Z)- and (4Z,8E)-4,8-tridecadienoate (cis:trans ratio of 94:6 at C-8). The isomeric ratio is established by converting an aliquot of the diene ester to the bis-epoxide using excess m-chloroperbenzoic acid and then gas-liquid chromatographic analysis of the bis-epoxide.

EXAMPLE 6

The 413 mg. of triphenylamylphosphonium bromide in 10 ml. of ether, under nitrogen and at room temperature, is added 0.57 ml. of n-butyllithium (1.67M in hexane). After 1.5 hours stirring, 120 mg. of ethyl (4Z)-8-oxo-4-octenoate in about 0.5 ml. ether is added. After about 2 hours at room temperature, the reaction is quenched by adding water. The reaction is worked up as in Example 5 and distilled (55° at 0.05 mm.) to yield ethyl (4Z,8Z)- and (4Z,8E)-4,8-tridecadienoate (cis:trans ratio of 78:22 at C-8).

EXAMPLE 7

To 310 mg. of triphenylamylphosphonium bromide in 5 ml. ether at 0°, under nitrogen, is added 0.43 ml. of 1.67M n-butyllithium in hexane. After about 0.5 hours, the solution is cooled at −78° and 88 mg. of ethyl (4Z)-8-oxo-4-octenoate in 0.5 ml. ether is added. The reaction mixture is stirred for 1 hour and then 5 ml. of ethanol is added slowly and temperature allowed to warm to −40° over 1.5 hours. After an additional 1.5 hours at −40°, the reaction mixture is warmed to room temperature over 2 hours and then quenched with water. The reaction is worked up as in Example 5 to yield ethyl (4Z,8Z)- and (4Z,8E)-4,8-tridecadienoate (cis:trans ratio of 27:73 at C-8).

EXAMPLE 8

The process of Example 2 is followed using each of methanol and isopropanol in place of ethanol to prepare methyl (4Z)-8-oxo-4-octenoate and isopropyl (4Z)-8-oxo-4-octenoate, respectively.

EXAMPLE 9

The bromide (VA; X is bromo) is prepared by stirring the mesylate of Example 3(C) with 1.5 equivalents of sodium bromide in dimethylformamide at room temperature and then worked up as in Example 3(D).

We claim:
1. A compound of the formula:

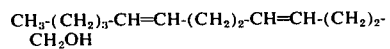

having cis isomerism at position C-4 and a mixture of cis and trans isomerism at position C-8.

* * * * *